United States Patent [19]

Smida et al.

[11] Patent Number: 5,824,479
[45] Date of Patent: Oct. 20, 1998

[54] INTER-LINE-PCR

[75] Inventors: Jan Smida, Freising; Stefan Leibhard, Oberschleissheim; Ludwig Hieber, Kirchheim; F. Eckardt-Schupp, Pfaffenhofen, all of Germany

[73] Assignee: Forschungszentrum fur, Umwelt und Gesundheit GmbH, Oberschleissheim, Germany

[21] Appl. No.: 646,809

[22] Filed: May 21, 1996

[30] Foreign Application Priority Data

May 22, 1995 [DE] Germany ............... 195 18 769.5

[51] Int. Cl.$^6$ ............... C12Q 1/68; C12P 19/34; C07H 21/04
[52] U.S. Cl. ............... 435/6; 536/24.3; 536/22.1; 435/91.2
[58] Field of Search ............... 536/22.1, 24.3; 435/91.2, 6

[56] References Cited

PUBLICATIONS

Versalovic et al., Genomic Fingerprinting of Bacteria Using Repetitive Sequence–Based Polymerase Chain Reaction, 1994, vol. 5, pp. 25–40.

Versalovic et al., DNA Fingerprintin of Pathogenic Bacteria by Fluorophore–Enhanced repetitive Sequence–Based Polymerase Chain Reactopm, 1995, Arch Pathol. Lab Med. vol. 119, pp. 23–29.

Pascale et al., Amplification of an ancestral mammalian L1 family of long interspersed repeated DNA occurred just before the murine radiation, Proc. Natl. Acad. Sci., vol. 87, Dec. 1990, pp. 9481–9485.

Chemical Abstract, vol. 115, 1991, p. 296, Abstract No. 115:272590v.

Chemical Abstract, vol. 117, 1992, p. 156, Abstract No. 117:246184n.

Chemical Abstract, vol. 120, 1994, p. 326, Abstract No. 120:976646.

Chemical Abstract, vol. 118, 1993, p. 562, Abstract No. 118:56972r.

Frothingham et al., A PCR–Based Method of Identifying Species–Specific Repeated DNAs, BioTechniques, vol. 13, No. 2, 1992, pp. 210, 212, 213.

Furano et al., Amplification of the Ancient Murine Lx Family of Long Interspersed Repeated DNA Occurred During the Murine Radiation, J. Mol. Evol., vol. 38 (1994), pp. 18–27.

Pascale et al., The Evolution of Long Interspersed Repeated DNA (L1, LINE 1) as Revealed by the Analysis of an Ancient Rodent L1 DNA Family, J. Mol. Evol. (1993), vol. 36 ppl 9–20.

Gong et al., COMMUNICATION Identification of Region–Specific Cosmid Clones by Hybrodization with Pooled Alu–LINE Polymerase Chain Reaction Products of Yeast Artificial Chromosone Clones, Methods in Mol. and Cell. Biol. (1994), 4:269–272.

Laten and Morris, SIRE–1, a long interspersed repetitive DNA element from soybean with weak sequence similarity to retrotransposons: initial characterization and partial sequence, Gene, vol. 134 (1993), pp. 153–159.

(List continued on next page.)

Primary Examiner—Kenneth R. Horlick
Assistant Examiner—Joyce Tung
Attorney, Agent, or Firm—Lowe, Price, LeBlanc & Becker

[57] ABSTRACT

The invention discloses novel oligonucleotides, which can be employed as primers in a polymerase chain reaction. Further a method for performing an IL-PCR using these oligonucleotides is disclosed. The oligonucleotides are suitable for the identification and taxonomic characterization of prokaryotic and eukaryotic microorganisms at the level of genus, species, and strain as well as for the identification and construction of transformation and tumour markers, respectively, for the application in medical cancer diagnostics.

24 Claims, 16 Drawing Sheets

OTHER PUBLICATIONS

Amariglio et al., *Identity of rearranged LINE/c–MYC junction sequences specific for the canine transmissible venereal tumor*, Proc. Natl. Acad. Sci. (USA), vol. 88, Sep. 1991, pp. 8136–8139.

Sambrook et al., *Molecular Cloning: A Laboratory Manual; Second Edition*, Cold Spring Harbor Laboratory Press, New York, 1989, pp. 2.72, E.3, E.4.

Simmler et al., *Adaptation of the Interspersed Repetitive Sequence Polymerase Chain Reaction to the Isolation of Mouse DNA Probes form Somatic Cell Hybrids on a Hamster Background*, Genomics 10, (1991), PP. 770–778.

Nelson et al., *Alu polymerase chain reaction: A method for rapid isolation of human–specific sequences from complex DNA sources*, Proc. Natl. Acad. Sci. (USA) Sep. 1989, vol. 86, pp. 6686–6690.

Ledbetter et al., *Rapid Isolation of DNA Probes within Specific Chromosome Regions by Interspersed Repetive Sequence Polymerase Chain Reaction*, Genomics 6 (1990), pp. 475–481.

Zietkiewic, *Genome Fingerprinting by Simple Sequence Repeat (SSR)–Anchored Polymerase Chain Reaction Amplification*, Genomics 20 (1994), pp. 176–183.

Munroe et al., *IRE–Bubble PCR: A Rapid Method for Efficient and Representative Amplification of Human Genomic DNA Sequences from Complex Sources*, Genomics 19 (1994), pp. 506–514.

Richard et al., *Integration of A Vector Containing A Repetitive LINE–1 Element in the Human Genome*, Molecular and Cellular Biology, Oct. 1994, pp. 6689–6695.

Hattori et al., *L1 Family of repetitive DNA sequences in primates may be derived from a sequence encoding a reverse transriptase–related protein*, Nature vol. 321, Jun. 1986, pp. 625–628.

Mathias et al., *Reverse Transcriptase Encoded by a Human Transposable Element*, Science vol. 254, Dec. 1991, pp. 1808–1810.

Katzir et al., *"Retroposon" insertion into the cellular oncogene c–myc in canine transmissible venereal tumor*, Proc. Natl. Acad. Sci. (USA), vol. 82, Feb. 1985, pp. 1054–1058.

Miki et al., *Disruption of the APC Gene by a Retrotransposal Insertion of L1 Sequence in a Colon Cancer*, Cancer Res. 52, Feb. 1992, pp. 643–645.

J.R. Miller, *Use of Porcine interspersed repeat sequences in PCR–mediated genotyping*, Mammalian Genome 5, (1994), pp. 629–632.

Servomaa and Rytomaa, *UV light and ionizing radiations cause programmed death of rat chloroleukaemia cells by inducing retropositions of a mobile DNA element (L1Rn)*, Int. J. Radiat. Biol., 1990, vol. 57, No. 2, pp. 331–343.

FIG. 3

PRIMER GF

GAAGGGTCTTTGCCAAACTC

ALIGNMENT

```
              3290        3300        3310
5'  Rat  GATGGATCACTACCGAATAC              3'
    K18  GAAGGGTCTTTGCCAAACTC
    Ks9  GAAGGGTCTTTGCCAAACTC
    J11  GAAGGGTCTTTGCCAAACTC
    J4   GAAGGATCTTTGCCAAACTC
    s8   AAAGGATCACTGCCAAACTC
    C14  GAAGGGTCTTTGCCAAACTC
    Ham  CAAGGGTCATTGCCGAAGGC
```

PRIMER GR
= GF INVERTED, COMPLEMENTED

GAGTTTGGCAAAGACCCTTC

FIG.4

PRIMER GF
CCATGTCTATCTCCATGCAC

ALIGNMENT

```
            4640       4650
5' Rat  CCATGCTTGTCACCCTGTAC   3'
   J4   CCATGTCTGTTGCCATGGAT
   K18  CCATGTCTATCTCCTTGCAC
   J11  CCATGTCTATCTCCATGCAC
   SK9  CCATATCTATCACCATGCAC
   Ham  CCCTGTCTATCACCATGCAC
```

PRIMER GR
= GF INVERTED, COMPLEMENTED
GTGCATGGAGATAGACATGG

FIG.6

INTER-LINE-PCR

The present invention relates to new oligonucleotide sequences, a method for performing an Inter LINE PCR using oligonucleotides having said sequences and the use of the oligonucleotides as a primer for Inter LINE PCR, especially for the discrimination of DNA of the members of the prokarya, archaea or eukarya or genetically altered organisms thereof.

By the polymerase chain reaction (PCR) one defined DNA fragment may be amplified from a complex DNA mixture using flanking complementary oligonucleotides, socalled primers. As a prerequisite the sequence to be amplified must be known. In contrast, when primers of short random sequences are used in PCR, a number of unknown DNA segments may be amplified from genomic DNA. Then the different amplified DNA fragments may be gel electrophoresed and are available for further analysis. This technique increasingly used recently has been referred to as arbitrary PCR (AP-PCR) (overview Tab. 1). The informational content of such a PCR application may be increased substantially, when primer sequences derived from repetitive DNA elements wide spread in the genome are used instead of randomly selected primer sequences (Nelson et al., 1989; Ledbetter & Nelson, 1991; Munroe et al., 1994; Zietkiewicz et al., 1994).

LINEs ("long interspersed elements") are a class of such repetitive DNA elements scattered in the genome having 100.000 copies per mammalian genome. A complete LINE sequence consists of about 6.300 base pairs; however, most elements existing in the genome are truncated. In total they represent about 10% of the DNA of the mammalian genome (Richard et al., 1994). The complete LINE sequence includes two open reading frames (ORFs), with ORF2 coding for reverse transcriptase, a retroviral polymerase (Hattori et al., 1986; Matthias et al., 1991). The existence of the reverse transcriptase as well as further structural and functional similarities with retrotransposons indicate the viral origin of this elements. As well as retroviruses complete LINEs also have the capability of duplicating transposition (Katzir et al., 1985; Miki et al., 1992). LINE related sequences are wide spread in the animal and plant kingdom, and the distinct sequence homology thereof among different species suggests a high evolutionary age of those elements. Their mobility is strictly regulated, which has resulted in a species specific distribution in the genome during evolution. On the other hand, increased activation of the transposition may be initiated by DNA damage or cellular stress; and this results in an altered number and distribution of LINEs in the genome (Servomaa & Rytömaa, 1990).

It is an object of the present invention to provide oligonucleotide sequences suitable for analysis and characterization of the genomes of different species as well as for the construction of markers for tumour diagnostics.

This object is met according to the present invention by providing oligonucleotide sequences selected from one or more of the following sequences:

1. GAA GGG TCT TTG CCA AAC TC (SEQ.-ID.-No. 1)
2. GAG TTT GGC AAA GAC CCT TC (SEQ.-ID.-No. 2)
3. CCA TGT CTA TCT CCA TGC AC (SEQ.-ID.-No. 3)
4. GTG CAT GGA GAT AGA CAT GG (SEQ.-ID.-No. 4)
5. GGC TGC CTT TAT ATG TTA CTG GCC (SEQ.-ID.-No. 5)
6. GGA GTG CTG ACT CAT ACA GCC TCC (SEQ.-ID.-No. 6)
7. CCT GTC TAG TGG TGA GAG TGG TG (SEQ.-ID.-No. 7)

The object of the invention is also met, in that said oligonucleotide sequences are shortened by one or more nucleotides at the 3'-terminus and/or the 5'-terminus.

However, the shortened sequences should comprise at least 15 nucleotides. The shortening preferable is carried out at the 5'-terminus, however, shortenings at the 3'-terminus are also possible. The shortening may occur at the 3'-terminus or 5'-terminus or both ends.

In a further embodiment of the invention the 5'-terminus of the oligonucleotide sequences is modified. The modifications of the oligonucleotide sequences of the present invention may be selected from any modification known in the prior art. Preferred modifications comprise the linking of the oligonucleotides at the 5'-terminus with amino acids, digoxigenin, biotin and further additional nucleotides. Preferably these further additional nucleotides create one or more recognition sites for restriction endonucleases.

The invention also comprises such oligonucleotide sequences exhibiting homology to the above seven oligonucleotide sequences, which at $\geq 80\%$. Preferably the homology is $\geq 90\%$, especially preferred $\geq 95\%$, and in a particular embodiment $\geq 97\%$.

As stated above, the oligonucleotides of the present invention may be modified in various manners. Preferably, the modifications should be performed in that the proportion of the guanine and cytidine nucleotides remaining in the oligonucleotides is $50\% \pm 5\%$.

The invention also comprises any vector systems known in the prior art containing the oligonucleotide sequences of the present invention.

The oligonucleotide sequences provided according to the invention are employed in a polymerase chain reaction. Such a polymerase chain reaction is referred to as Inter-LINE-PCR, which is abbreviated as IL-PCR. The performance of IL-PCR at least comprises following process steps:

a) Mixing the DNA to be analyzed with one or more of the oligonucleotides having an aforementioned sequence (SEQ ID NO. 1–7) in a reaction buffer suitable for the perfomance of a PCR reaction, and optionally further additives;

b) Performance of amplification steps comprising several denaturations and renaturations for obtaining amplified DNA products; and c) Separation and analysis of the amplification products.

From a number of publications the performance of polymerase chain reaction is well known to those skilled in the art. See for example the publications in the reference list enclosed herein. The polymerase chain reaction is permitted to be modified to optimize the conditions of the process for a specific application. Such optimizations are easily to be performed by those skilled in the art without further inventive steps and are encompassed by the present invention.

Preferably, the IL-PCR performed with the oligonucleotide sequences provided according to the present invention comprises as amplification steps, an initial denaturation step, one or more low stringency denaturations and renaturations and several higher stringency denaturations and renaturations, and a final chain elongation step.

Preferably, 3–7 low stringency denaturations and renaturation steps and 20–30 higher stringency denaturations and renaturation steps are performed.

The reaction buffers for performing the PCR reaction are known to those skilled in the art and may be conventionally adapted to the requirements of the experiment to be performed. Preferably, the reaction buffers contain a viscosity increasing agent, with gelatin being especially preferred.

The analysis of the PCR products is carried out by ordinary separation processes known to those skilled in the art, such as for example agarose gel or polyacrylamide gel.

The oligonucleotides provided according to the present invention are employed as primers for an Inter LINE polymerase chain reaction. It is possible to characterize or discriminate DNA of the prokarya, archaea or eukarya or genetically altered organisms thereof by using the oligonucleotides of the present invention in a PCR reaction. For example discrimination and characterization, respectively, of unique taxa and phyla of the prokarya, archaea or eukarya is possible. For example, yeasts and bacteria are distinguishable by the IL-PCR method of the present invention.

In a further preferred embodiment the oligonucleotides provided according to the invention are employed in order to distinguish tumor cells from normal cells. Transformation and/or tumor markers may be constructed and identified by the method of the present invention. Accordingly, the oligonucleotides provided according to the invention are employed preferably in tumor diagnostics. Further fields of employment and applications are mentioned in the following exemplified embodiments.

The oligonucleotide sequences, which can be used in an Inter LINE PCR result from performing at least following steps:
1. Selecting of any LINE sequence;
2. Alignment of said LINE sequences;
3. Creation of consensus sequences from conserved segments of these LINE sequences by selecting such areas, which meet the following criteria:
   a) at least 20 base pairs with homology values to LINE sequences $\geq 80\%$, preferably $\geq 90\%$;
   b) a CG:AT ratio of $\geq 1$;
   c) GC rich 5' and 3' termini; and
   d) selecting such nucleotides appearing most frequently in the vertical plane of the alignment.

Preferably, the LINE sequences are defined in that they exhibit two open reading frames (ORFs), which encode a reverse transcriptase and a retroviral polymerase or parts thereof. Also LINE sequences with other characteristics can be employed.

Thus, the technique developed according to the invention, the socalled Inter LINE PCR (IL-PCR), may be used for the analysis and characterization of genomes of different species in a surprisingly superior manner.

The primers used were derived from mammalian DNA sequences and were originally used for the analysis of mammalian genomes, since species specific reproducible patterns of the fragments amplificated via PCR with any primer could be produced for various cell lines, e.g. of hamster, mouse, human etc. Amongst certain conditions the same primers are also suitable for the characterization and identification of lower eukaryotes (such as yeasts), archaebacteria, and prokaryotes, although no LINE related sequences are known among the archaebacteria and prokaryota. Following electrophoresis of IL-PCR products specific band patterns emerge, by which also closely related genera, species or phyla may be discriminated.

Following a preceding sequence analysis and comparison of the sequences, PCR primers for microorganisms covering specifically defined taxa may be specifically synthesized. The field of application of this method is so extensive, that members of the three domaines bacteria, archaea and eukarya can be covered and on the other hand even closely related species discriminated by employment of conservative primers. Using hybridization techniques and/or specific PCR a routinely employment for the identification of most different organisms and cell cultures is rendered possible.

In contrast to techniques established up to now, listed in Table 1, organisms may be identified and characterized at different taxonomic levels, for example genus, species and phylum. All other methods are limited to one or two of said levels.

The invention is now illustrated in more detail with respect to the enclosed figures.

BRIEF DESCRIPTION OF THE FIGURES

FIG. 3: Alignment of several LINE homologous clones in the range of the rat LINE sequence pos. 3320–3346.

FIG. 4: Sector of alignment for the construction of primers GF and GR.

FIG. 6: Sector of alignment for the construction of primers RF and RR.

GENERAL DESCRIPTION OF THE INVENTION

Within the framework of a research project for clarification of the molecular mechanisms of the carcinogenesis by radiation the implications of genetic alterations in neoplastically transformed embryonic fibroblasts of the Syrian hamster (SHE cells) was to be investigated. For this purpose libraries of genomic DNA of normal (nontransformed) and of transformed cells were constructed and the DNA libraries compared using differential hybridization. Clones, which were overrepresented or underrepresented, respectively, in one of the libraries were isolated and sequenced. As a result a number of genes relevant for the carcinogenesis could have been isolated. In this analysis surprisingly much clones having LINE homologous sequences could have been isolated.

Several universal primers were derived from the consensus sequence of said LINE clones, which were employed single or in combination in the Inter LINE PCR. First, DNA from SHE cells, subsequently also DNA from different other mammalian species were used for the amplification. The electrophoresis of amplificates in agarose and polyacrylamide gels, respectively, revealed charasteristic band patterns of the length ranging between 100 and 5000 bp, which evidently are organism specific.

It could be demonstrated according to the invention, that specific band patterns emerge under suitable PCR conditions, even with lower eukaryotes (yeasts) and with prokaryotes such as bacteria (*E. coli*, different soil bacteria as well as the fast evolving planctomycetes) and with archaea, although these organisms are not known to have LINEs up to now. Particularly, it could be demonstrated, that this technique is suitable for the differentiation of different yeast species being employed for example in the brewery technology, winegrowing or in the bakery. It is also possible to detect detrimental prokaryotes appearing in the brewery technology as trace contaminations and to identify the causing pests.

In enlargement of the original work it could be additionally demonstrated, that by detailed analysis the band patterns of PCR products of normal and tumourigenic mammalian cell lines are distinguishable in detail. Variations of the band patterns (missing, additional or bands varying in length) may serve as indicators in the diagnosis of early events in the tumour development, as it is demonstrated by the example of radiation induced transformants of the syrian hamster embryonal fibroblasts.

Figure 1:
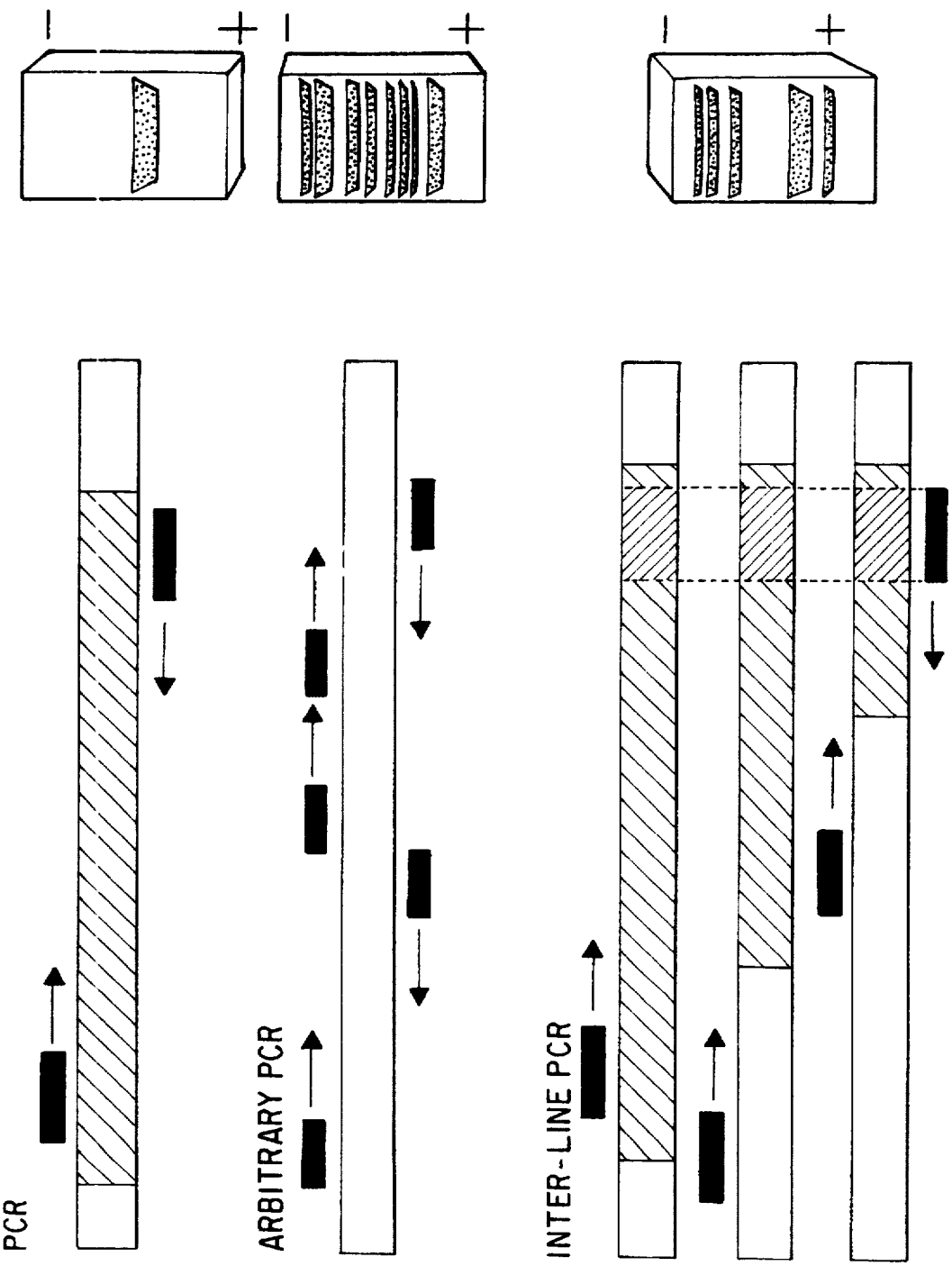
FIG. 1: Comparison of different PCR applications.

FIG. 1 illustrates schematically Inter LINE PCR in comparison with classical PCR applications. The gray shaded bars represent areas of known base sequence. The direction of synthesis of the polymerase (starting from the respective primer) is marked by arrows. At the right-hand side of the drawing the expected PCR products were separated schematically on agarose gels. Special emphasis is made to the quality differences of the amplification products of the AP-PCR application compared to the Inter LINE PCR. The Inter LINE PCR products partly consist of known sequence areas. Therefore, said products are made available for further molecular biological analysis.

DETAILED DESCRIPTION OF THE INVENTION

In the following, the invention is described in detail with respect to several application examples, without limiting the application of this technique thereto.

A. Basic works, which are identical and a prerequisite, respectively, for all applications described a) Construction of genomic DNA libraries EcoRI restriction enzyme digested syrian hamster embryonal fibroblast (SHE cells) total genomic DNA was cloned into the lambda gt 11 vector. The proliferation of recombinant phages occured in the Y1088 derivative strain of *E. coli* K12 (Pharmacia Freiburg). Cloning and packaging of the phages was conducted according to standard molecular biological methods (Sambrook et al., 1989).

b) Differential hybridizing of recombinant clones

In each case about 1000 recombinant phage clones were plated employing the "overlayer" technique (Sambrook et al., 1989). Two identical "plaque blots" per plate were produced. Then these were successively hybridized with homologous (from normal SHE cells) and heterologous (tumour SHE cells) genomic DNA probes. Recombinant clones exhibiting striking differences in hybridization property were isolated. Also, in parallel to the technique described above, total mRNA cDNA probes of both the cell lines to be compared were employed as hybridization probes, with isolating all clones showing hybridization signals.

c) Characterization of recombinant clones

Figure 2:
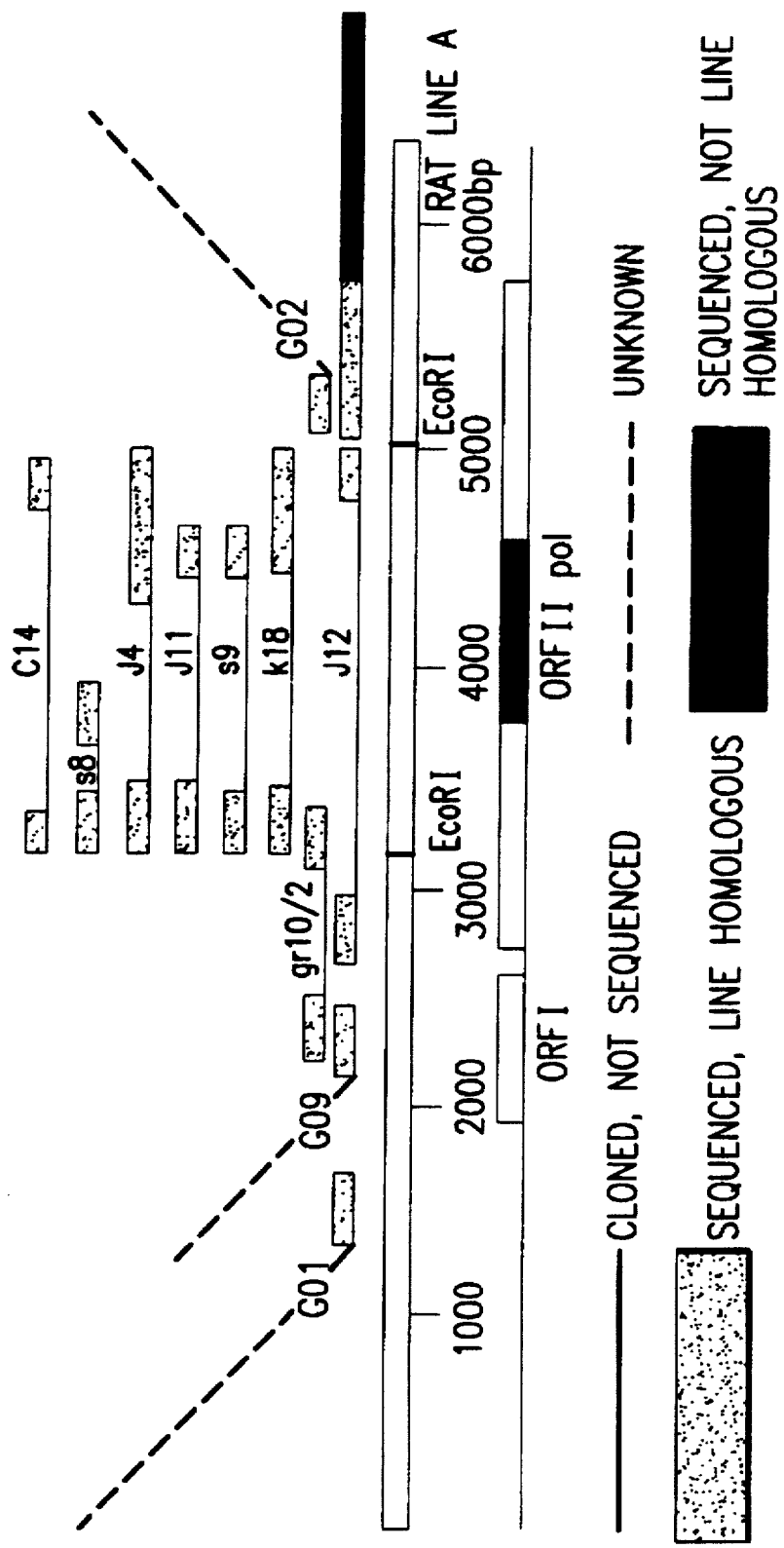
FIG. 2: Position of LINE homologous clones to the rat LINE sequence.

Twenty of the clones isolated in such a manner were sequenced using T7 polymerase and vector gt 11 specific primers (Pharmacia). Then the DNA sequences were analyzed using the HUSAR computer programme (DKFZ, Heidelberg) and compared to data bases (Genius gene bank, Heidelberg). Twelve of the 20 clones revealed significant agreement with already known rodent LINE sequences. In FIG. 2 these clones with their relative positions to the rat LINE DNA sequence (RNLINED, Genebank Heidelberg) are shown.

d) Construction of LINE specific PCR primers

It is evident from FIG. 2, that the majority of the isolated clones is homologous to the rat LINE sequence area, which is localized between the two EcoRI restriction sites and corresponds to the most conserved area of the LINEs. This area includes inter alia the sequence area being homologous to the reverse transcriptase. Sequences of such clones are partly illustrated in the figures. Alignment of these sequences, which was done using the HUSAR programme exhibits areas of differently strong developed similarities of the base sequence. Those areas showing highest homology values were examined for their capability for the construction of primers. For this selection following criteria were taken into account:

1. At least 20 base pairs with high similarity values.
2. CG:AT ratio should be at least 1 or more than 1, respectively.
3. The 5' and 3' termini of these areas should be GC rich to increase the relative binding energy of the designed primer at these sites.

Figure 3:
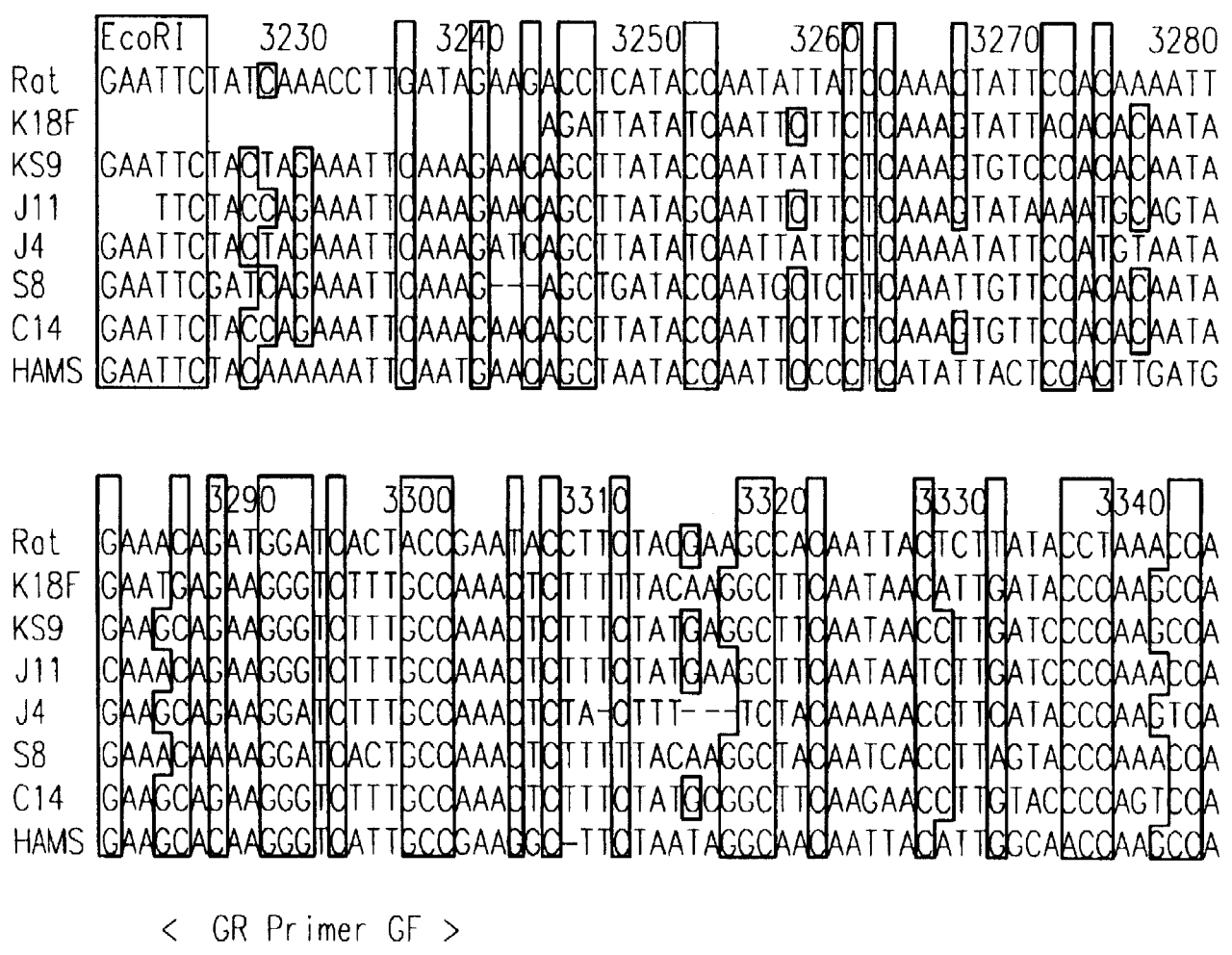

FIG. 3 demonstrates the alignment of sequences investigated in the area from the EcoRI restriction site (rat LINE position 3220–3226) to rat LINE position 3346. To illustrate the selection criteria for the contruction of primers the GC rich conserved positions were shaded gray.

Figure 5:
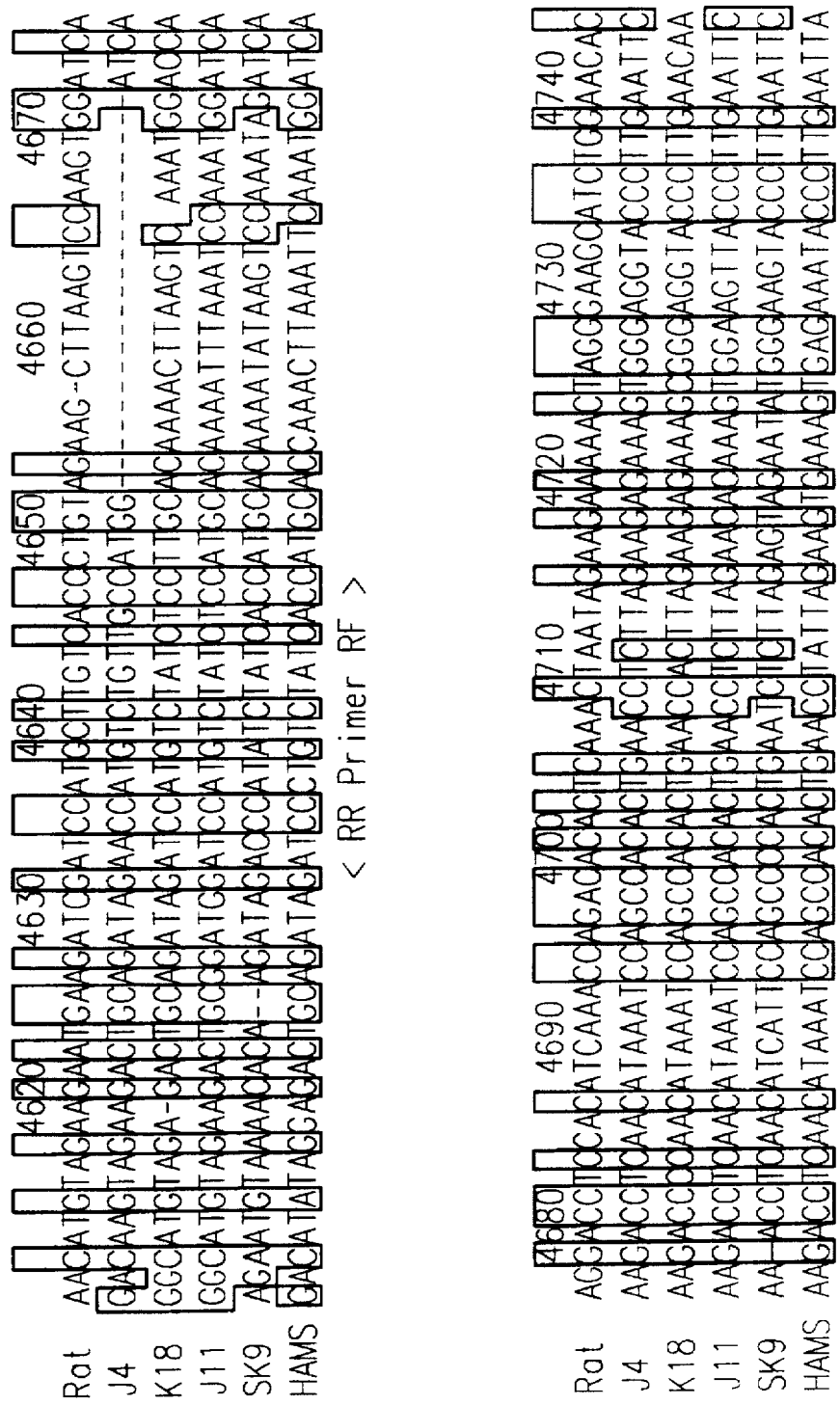
FIG. 5: Alignment of several LINE homologous clones in the range of the rat LINE sequence pos. 4611–4745.

In FIG. 4 the segment of the alignment, which meets best the criteria stated by us and thus was used for constuction of primers is illustrated. The homologous positions, i.e. those occupied by identical bases were shaded gray. Finally the consensus sequence and the corresponding inverted complementary sequence were used for the synthesis of the primer oligonucleotides. By analogy with the construction of the primers GF and GR the FIGS. 5 and 6 represent the construction of primers RF and RR which were constructed from the alignment in the range of 3290–3310 (rat LINE positions).

The following list contains primers, which were used single or in combination for IL-PCR. In addition to the consensus oligonucleotides already described, also those primers which were directly constructed from the sequences of several LINE clones and also meet our criteria were incorporated in this list. Shortened primers (e.g. GRshort) may be employed especially in the genomic analysis of prokaryotes.

| Name | Sequence | Origin |
| --- | --- | --- |
| GF | GAA GGG TCT TTG CCA AAC TC | consensus |
| GR | GAG TTT GGC AAA GAC CCT TC | consensus |
| GRshort | GAG TTT GGC AAA GAC CC | consensus |
| RF | CCA TGT CTA TCT CCA TGC AC | consensus |
| RR | GTG CAT GGA GAT AGA CAT GG | consensus |
| G01 | GGC TGC CTT TAT ATG TTA CTG GCC | LINE clone G01 |
| G02 | GGA GTG CTG ACT CAT ACA GCC TCC | LINE clone G02/G13 |
| G09 | CCT GTC TAG TGG TGA GAG TGG TG | LINE clone G09 | e) Inter LINE PCR

Reaction Conditions for the PCR Amplification

The reagents were employed in a total volume of 50 μl according to the manufacturer's description (GIBCO, BRL, Eggenstein). To the 10 fold PCR buffer 0.005% gelatin was added. In a 50 μl reaction assay 200 pMol oligonucleotide and 100 ng genomic DNA was used. The PCR reaction was carried out in the Hybaid heat block (MWG, Ebersberg).

| Amplification parameters | | |
| --- | --- | --- |
| First denaturation step: | 8 min | 93° C. |
| 5 lower stringency cycles: | 1 min 30 sec | 37° C. |
|  | 2 min | 72° C. |
|  | 1 min 30 sec | 93° C. |
| 25 higher stringency cycles: | 1 min | 52° C. |
|  | 1 min 30 sec | 72° C. |
|  | 1 min | 93° C. |
| Final chain elongation: | 10 min | 72° C. |

For control and analysis the amplification products were electrophoresed by 1% agarose gels and visualized by ethidium bromide staining.

Polyacrylamide Gel Electrophoresis

Non denaturating 6% PAA gels (9 ml acrylamide stock solution: 300 g acrylamide and 5 g N,N'-methylene bisacrylamide/1 H₂O; 0.9 ml ME buffer: 1M MOPS, 10 mM EDTA, pH 8.0; and 11.25 ml 40% glycerol fill up to a total volume of 45 ml with H₂O; +75 μl TEMED; +50 μl APS) were prepared on a hydrophilic carrier foil according to the specifications of the manufacturer (DIAGEN, Hilden). The electrophoresis was conducted in a temperature gradient gel electrophoresis apparatus (TGGE) of DIAGEN company, Hilden, with 1× MOPS running buffer, at a constant temperature of 25° C., 3–4 h at 200 V. The gels were stained with silver nitrate according to the protocoll of the DIAGEN co. and photographed.

B. Several examples for the application of the invention.

EXAMPLE 1

Identification of neoplastically transformed cell lines and derivation of transformation and tumour markers, respectively.

Syrian hamster neoplastically transformed cell lines and tumour cell lines established thereof in the nude mouse may be identified and distinguished from normal SHE cells by means of the Inter LINE PCR.

Figure 7:
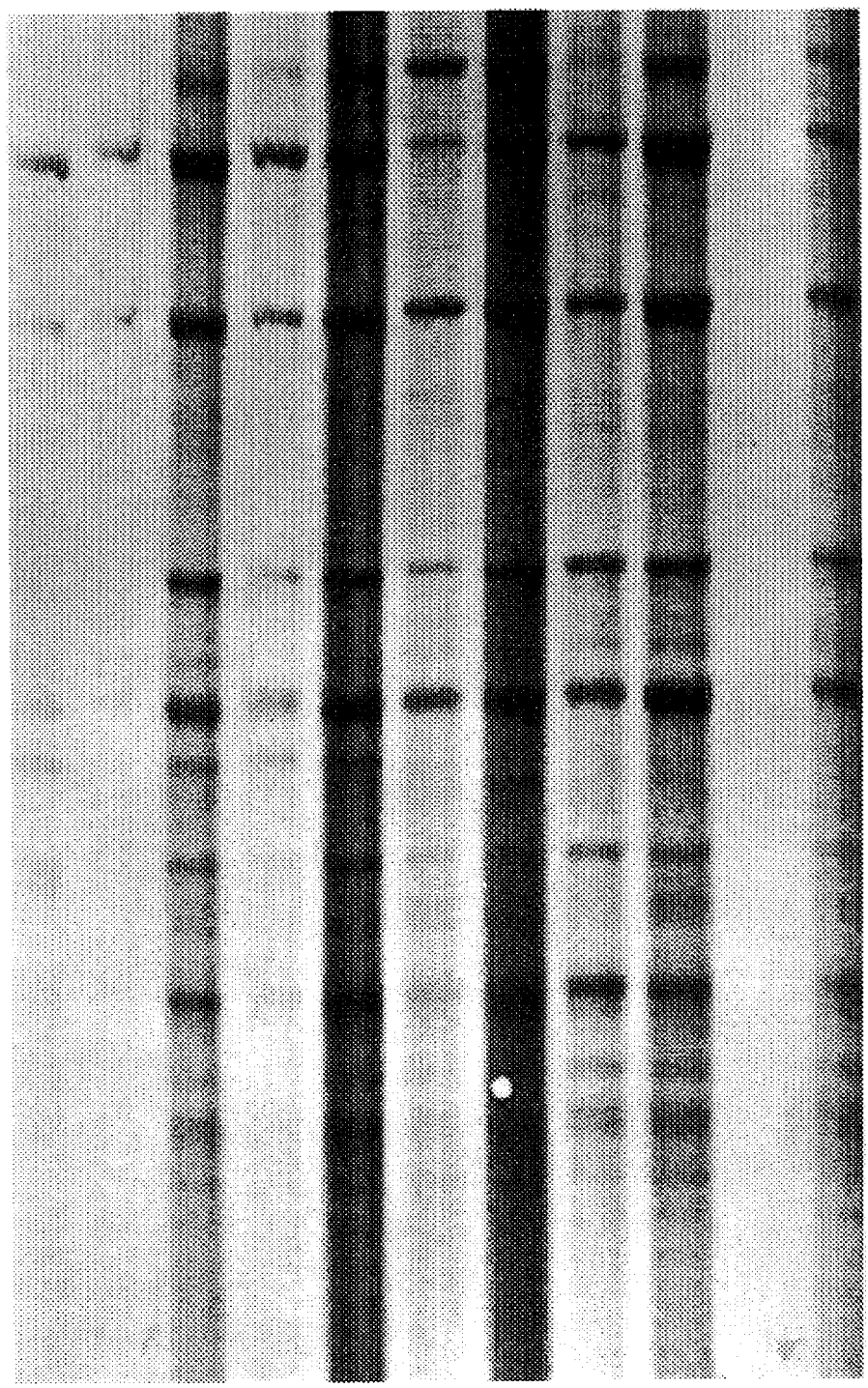
FIG. 7: Autoradiograph of the DNA fragments, which were prepared by employment of the primer GR of transformed and primary SHE cell lines by means of IL-PCR and were electrophoresed on polyacrylamide gel. In all investigated primary cell lines (lanes 7–11) a fragment (<) is found, which is missing from transformed cell lines (lanes 1–6).
Figure 8A:
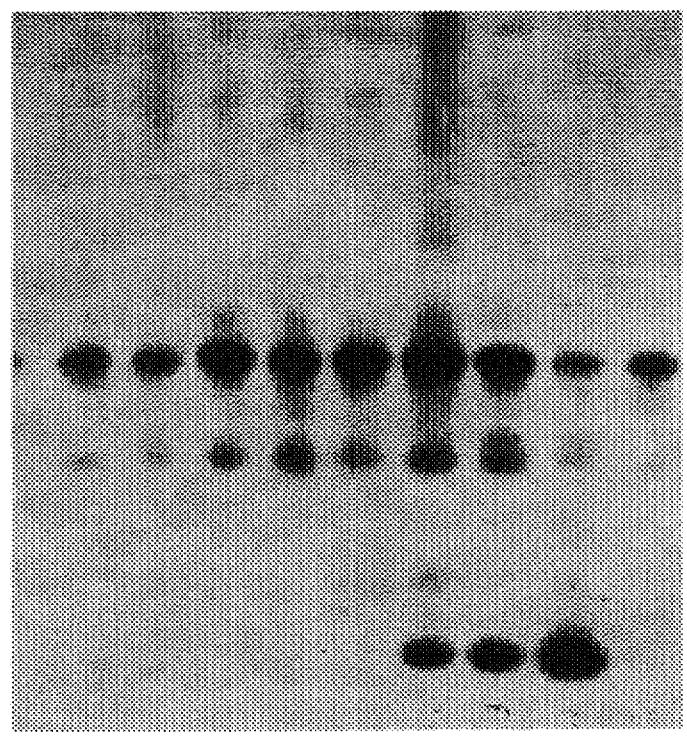
FIGS. 8A and 8B: The fragment of FIG. 7 specific for primary SHE cells was reamplified in a second PCR and used as a hybridizing probe for a Southern blot of an IL-PCR, which was electrophoresed on an agarose gel. Only the DNA from primary SHE cells exhibits a signal with increasing stringency of the hybridization (A: low stringency, B: high stringency).
Figure 8B:
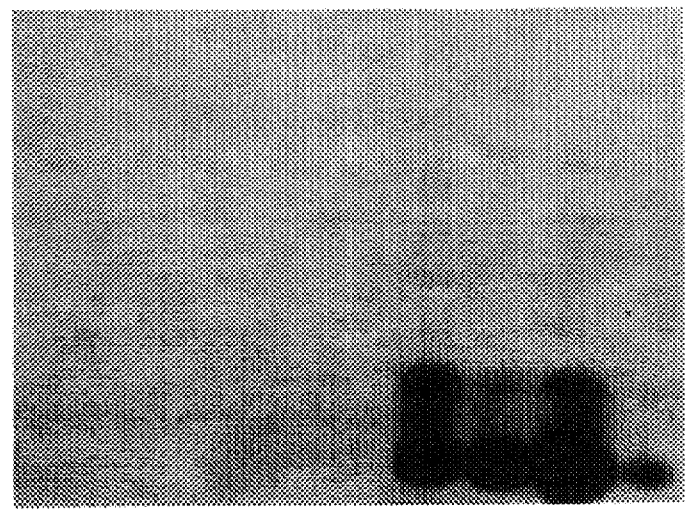

Syrian hamster primary embryonic fibroblasts were neoplastically transformed by exposition to ionizing radiation. If those transformed cell lines were injected into an athymic nude mouse, tumours develop; following their isolation tumour cell lines may be established thereof. Genomic DNA from the various cell lines was isolated using standard methods. Specific DNA fragments were amplified by Inter LINE PCR using the described primers. The amplificates were radiolabelled and electrophoresed on polyacrylamide gel. As illustrated in FIG. 7 transformed cell lines may be distinguished from normal SHE cells in this case by means of a missing or additional band, respectively. Then, this band was isolated, reamplified, radiolabelled and employed as a probe for a southern blot of the IL-PCR (FIG. 8). It is fundamentally valid, that band patterns of IL-PCR amplificates of the mammalian genome are very complex and undistinguishable on agarose gels; in contrast, tumour specific or transformation specific bands, respectively, may be recognized in the southern analysis (IL-PCR products, LINE clones as well as microsatellite probes may be employed as suitable probes), which may be used for the future as transformation or tumour marker, respectively, for diagnostic use after further characterization.

EXAMPLE 2

Differentiation of various mammalian species

Individual mammalian species can be distinguished by the band pattern of the PCR amplificates using Inter LINE PCR. For this purpose genomic DNA from animal tissue samples as well as DNA from established cell lines may be used.

The genomic DNA was isolated from the cell cultures or the tissue samples, respectively, by standard methods. The primers GF, GR, RF and RR were employed for the PCR amplification; the PCR conditions were as described in e).

Figure 9:
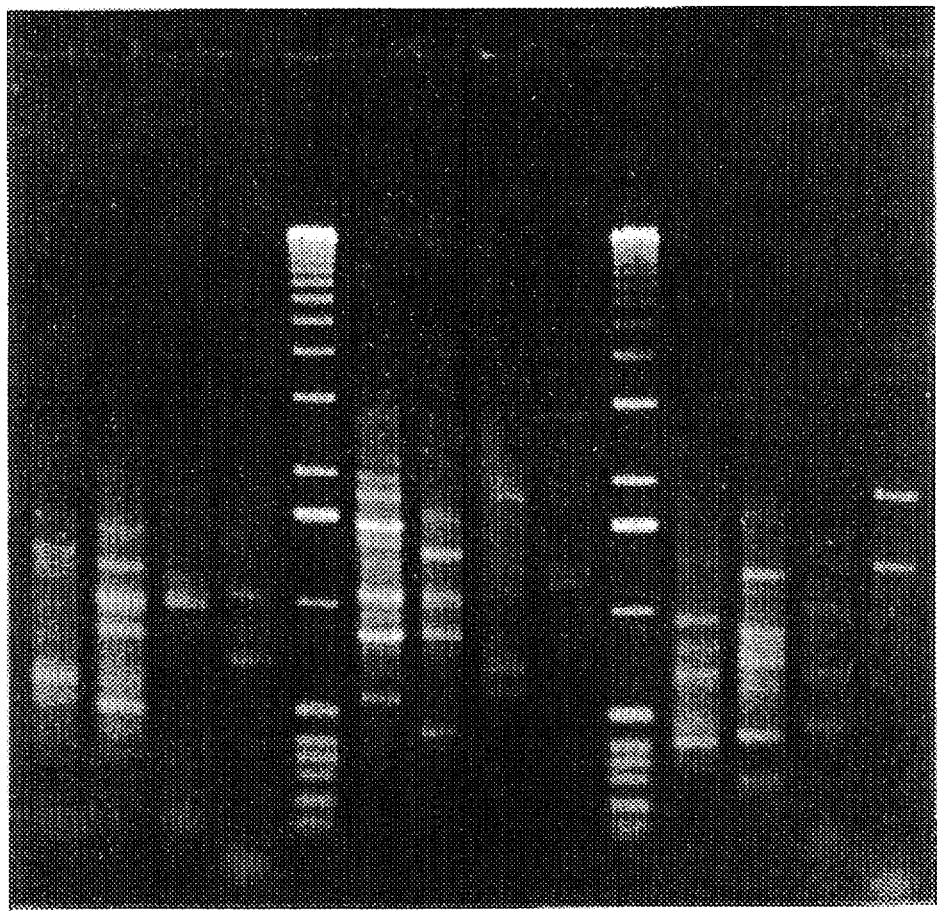
FIG. 9: Electrophoresis of IL-PCR amplificates with the primers GF (lanes 1, 6, 11), GR (lanes 2, 7, 12), RF (lanes 3, 8, 13) and RR (lanes 4, 9, 14) from DNA of hamster (lanes 1–4), mouse (lanes 6–9) and human (lanes 11–14). Lanes 5 and 10 contain size standards. Ethidium bromide staining.
Figure 10:
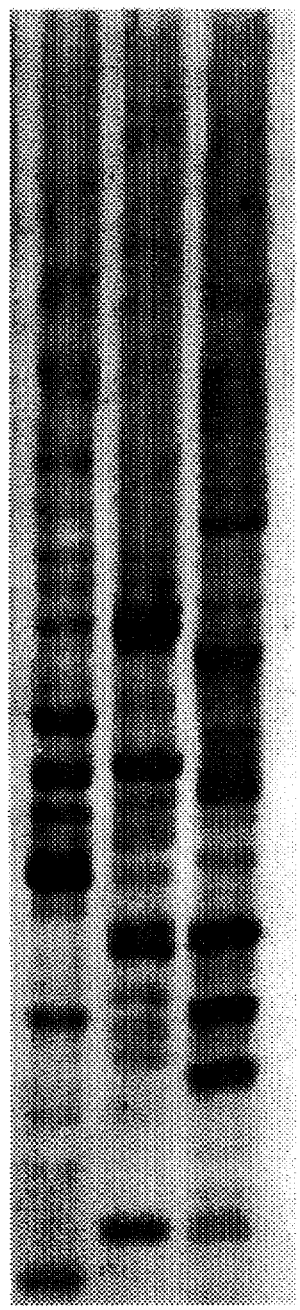
FIG. 10: The IL-PCR with the primer GR of hamster (left), mouse (centre), human (right) was electrophoresed on nondenaturating polyacrylamide gel. Silver nitrate staining.

The PCR amplificates were separated in agarose as well as in polyacrylamide gels. FIGS. 9 and 10 illustrate the clearly distinguishable hamster, mouse and human band patterns as examples.

EXAMPLE 3

Identification and discrimination of various yeast strains

The identification and differentiation of individual yeast strains by means of the invention of the IL-PCR is exemplary demonstrated for the useful and noxious yeasts relevant for the brewery technology.

Figure 11:
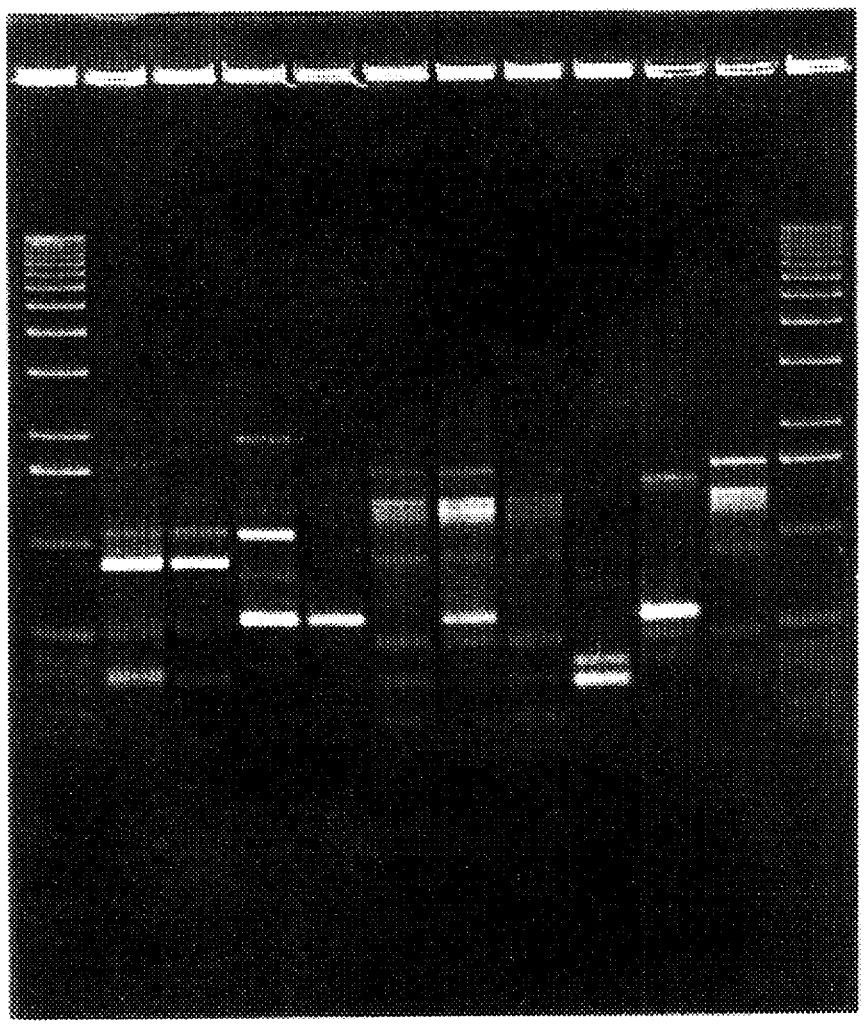
FIG. 11: IL-PCR amplificates with the primer GR and electrophoresis on agarose gel (lanes 1 and 12 contain size standards) of the following brewery relevant yeast strains: Lanes 2 and 3 two Zygosaccharomyces strains, lanes 6, 8 and 11 Saccharomyces cerevisiae strains, lane 9 Saccharomycodes ludwigii, lane 10 Saccharomyces bayanus, as well as two unknown yeast strains, lanes 4 and 5. Ethidium bromide staining.
Figure 12:
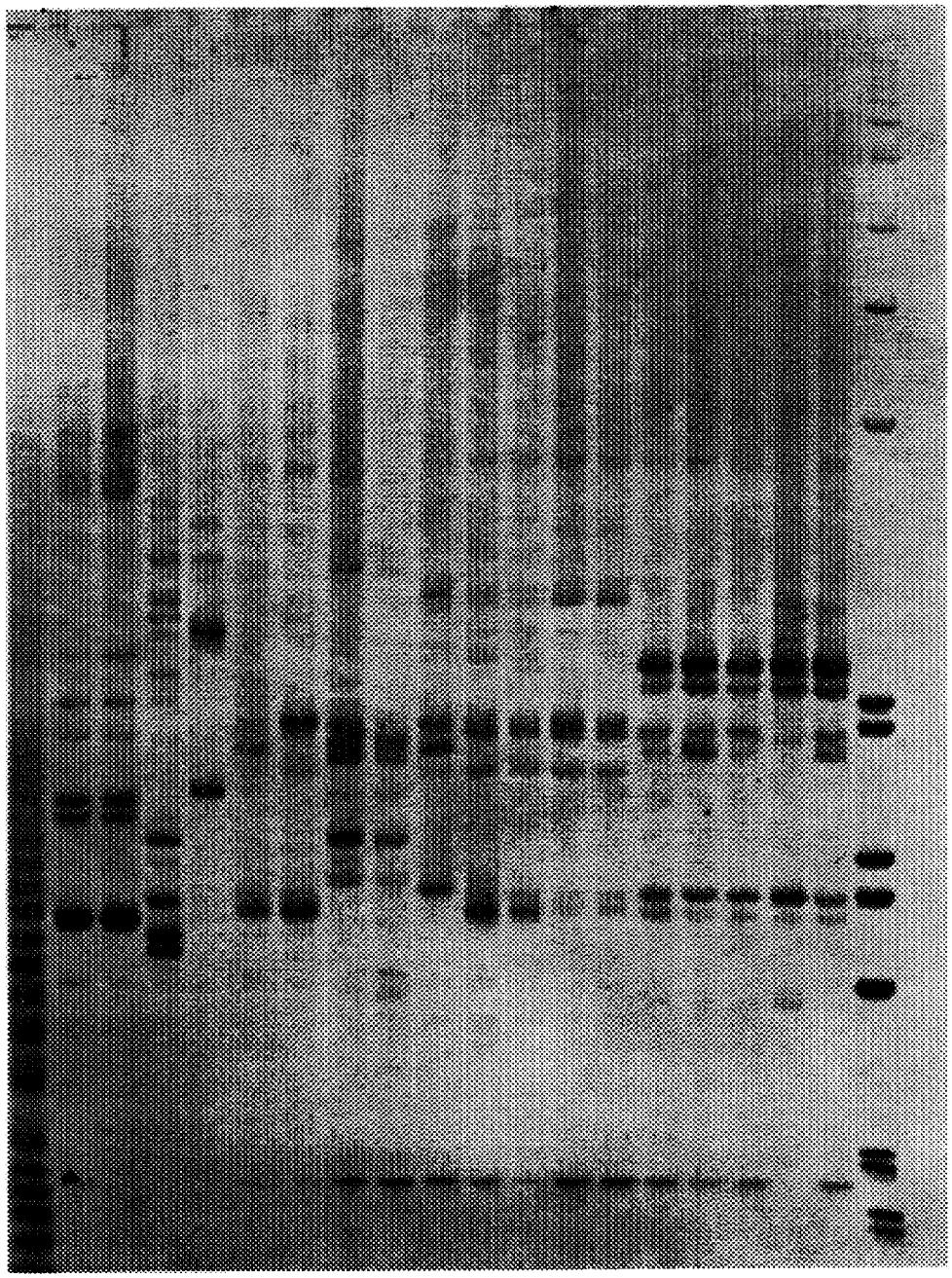
FIG. 12: IL-PCR amplificates with the primer GR were electrophoresed on a nondenaturating polyacrylamide gel (lanes 1 and 20 contain size standards). Lanes 6, 7, 11–14 contain top-fermented yeasts of the species Saccharomyces cerevisiae, lanes 15–19 bottom-fermented strains of the same species. Lanes 2–5, as well as 8–10 contain noxious yeasts of different species and genera. Silver nitrate staining.
Figure 13:
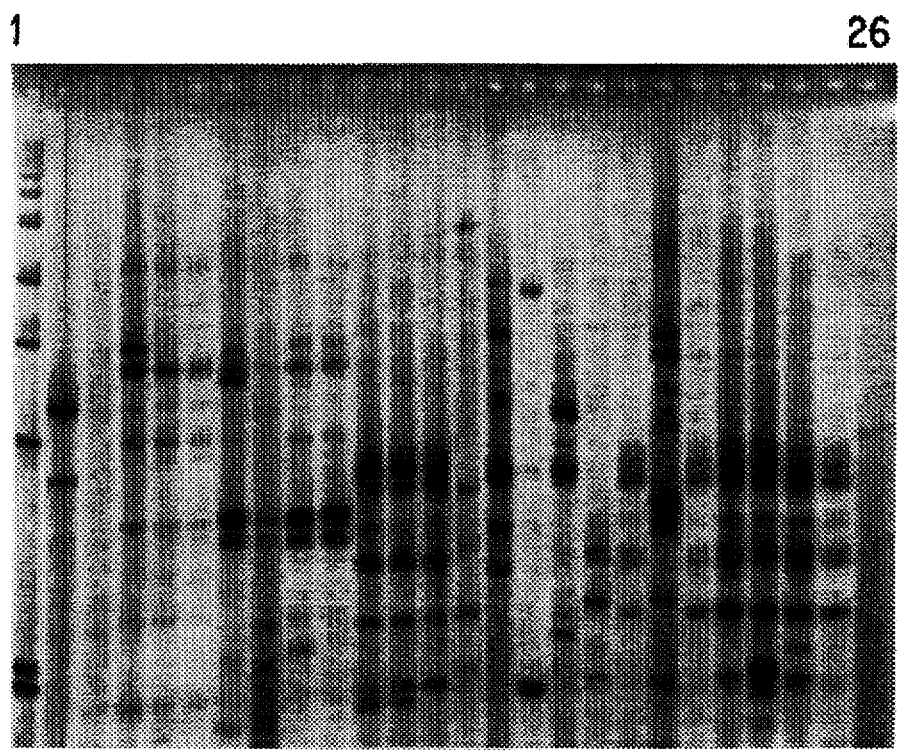
FIG. 13: IL-PCR amplificates of bacteria with the primer GR were electrophoretically separated on a nondenaturating polyacrylamide gel (lanes 1 and 26 contain size standards). Lanes 6, 7 and 11–14 contain different strains of the species Pediococcus damnosus. Lanes 10–25 refer to different species of the genus Lactobacillus (10–13 L. lindneri, 14 L. coryneformes, 15–25 L. brevis).

100 ng of yeast genomic DNA isolated according to standard protocolls were amplified in the Inter LINE PCR (see e)). The PCR amplificates of the same IL-PCR reactions were separated by agarose gels (FIG. 11) as well as polyacrylamide gels (FIG. 12, yeasts; FIG. 13, bacteria). By means of the different band patterns the investigated yeast and bacteria strains may be distinguished on the level of genus and species, in part also on strain level. For instance noxious yeasts in the beer brewing process may clearly be distinguished from the useful yeasts.

EXAMPLE 4

Taxonomic analysis of prokaryotes

Figure 14:
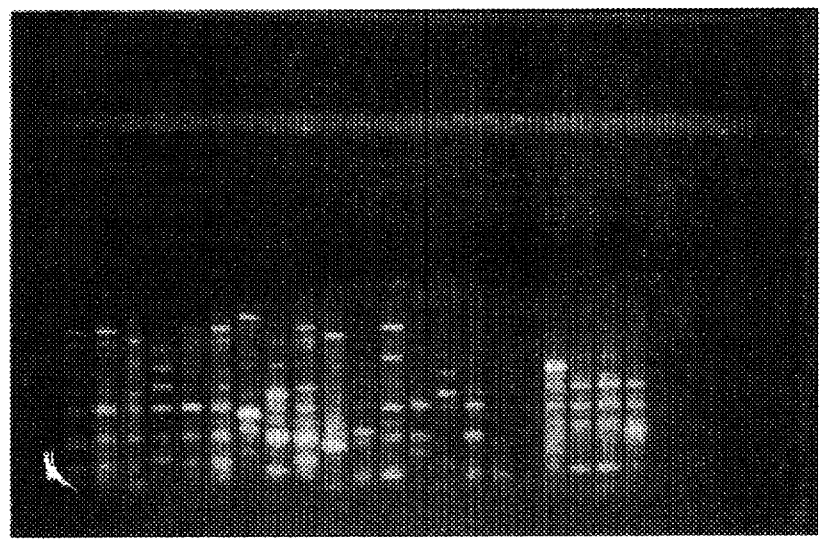
FIG. 14: IL-PCR amplificates of different new isolates of soil bacteria with the primer GRshort, electrophoresed on agarose gel. Lanes 1–11: new isolates of plant associated gram-negative bacteria, lanes 12–17: six well characterized species of the genus Burkholderia, lanes 18–21: new isolates of nitrogen fixing free living soil bacteria. Ethidium bromide staining.
Figure 15:
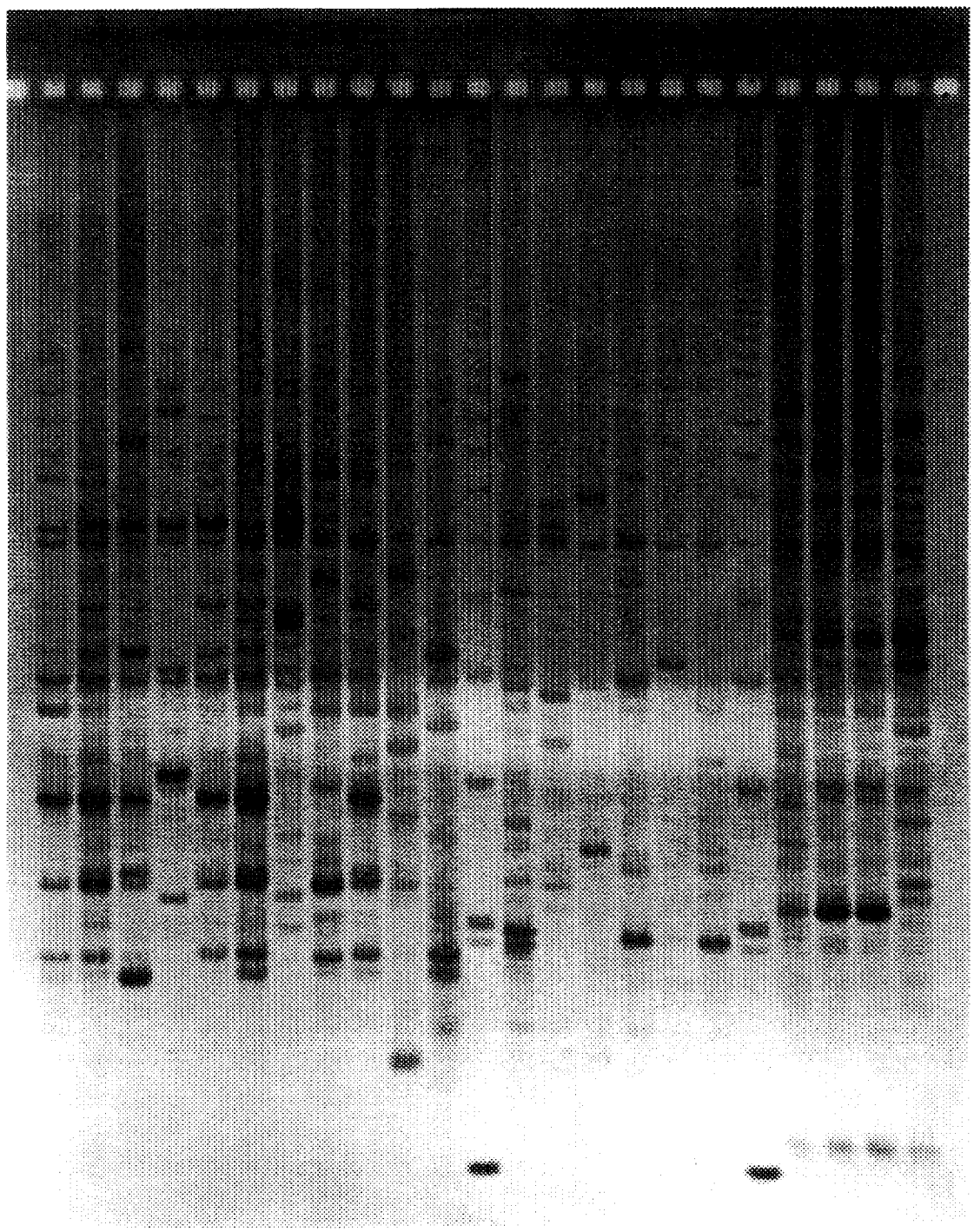
FIG. 15: The same IL-PCR amplificates as in FIG. 13 were electrophoresed on nondenaturating polyacrylamide gel. In lanes 12 and 19 size standards were applied. Silver nitrate staining.

The high applicability of the invention of the IL-PCR is demonstrated with regard to the identification and taxonomic classification of newly isolated soil bacteria. The genomic DNA from newly isolated soil bacteria of unknown species and genus was obtained according to standard methods (Sambrook et al., 1989). In this application a 3'-shortened oligonucleotide, GRshort, was employed as a primer for the IL-PCR. The PCR conditions were as described under e). For the analysis the amplificates were separated electrophoretically in 1% agarose gels (FIG. 14: a lot of new plant associated isolates from rice cultures were compared with already characterized type strains) and in polyacrylamide gels (FIG. 15: same IL-PCR as in FIG. 14). With respect to the band pattern, the new isolates may a) be sorted into taxonomic groups, b) parallel isolates may be detected and c) also be identified if the type is already known.

EXAMPLE 5

Detection of mycoplasma contamination in cell cultures of mammals

Figure 16:
FIG. 16: IL-PCR amplificates of 3 different mycoplasmas wherein Grshort and GR are used. Lanes from the left to the right show: 1 and 9, size standards; 2, L929-mice fibroblasts; 3, GRshort, *Mycoplasma orale*; 4, Grshort, *Mycoplasma argininii*; 5, Grshort, *Acholeplasma laidlawii*; 6, GR, *Mycoplasma orale*; 7 Gr, *Mycoplasma argininii*; 8, Grz, *Acholeplasma laidlawii*.

Mycoplasmas were isolated from nutrient medium of L929 mice fibroblasts infected with mycoplasmas; DNA was isolated according to standard methods (Sambrook et al, 1989). IL-PCR was conducted using oligonucleotides GRshort and GR, and amplificated sequences were separated on PAA-gels. A reproducible amplification of an IL-PCR product pattern typically for mycoplasmas could be detected (FIG. 16).

It could be illustrated by the above examples, that Inter LINE PCR is a method for identification and taxonomic characterization of prokaryotic and eukaryotic microorganisms at the level of genus, species, and strain as well as for the identification and construction of transformation and tumour markers, respectively, for the application in medical cancer diagnostics. The oligonucleotides and the method provided in the present invention can be used for medical diagnostics, for instance, for identification and construction of transformation and tumor markers, respectively, for the application in medical cancer diagnostics and for identification of relevant pathogenic bacteria and fungi (i.e. Candida species) in medical diagnostics.

In preferred embodiments of the invention the oligonucleotides provided in the present invention can be used for discriminating members of prokarya, archaea or eukarya; in particular single taxa and strains of prokarya, archaea or eukarya may be discriminated. For example yeasts and bacteria may be discriminated. Discrimination comprises identification and/or taxonomic characterization of these organisms.

---

We claim:

1. An oligonucleotide sequence selected from the group consisting of:

(1) GAA GGG TCT TTG CCA AAC TC (SEQ.-ID.-No. 1)

(2) CAC TTT CCC AAA CAC CCT TC (SEQ.-ID.-NO. 2)

(3) CCA TGT CTA TCT CCA TGC AC (SEQ.-ID.-No. 3)

(4) GTG CAT GGA GAT AGA CAT GG (SEQ.-ID.-No. 4)

(5) GGC TGC CTT TAT ATG TTA CTG GCC (SEQ.-ID.-No. 5)

(6) GGA GTG CTG ACT CAT ACA GCC TCC (SEQ.-ID.-No. 6) and (7) CCT GTC TAG TGG TGA GAG TGG TG (SEQ.-ID.-No. 7).

2. An oligonucleotide sequence according to claim 1, which is shortened at the 3' and/or the 5' terminus of the sequence and which comprises at least 15 nucleotides.

3. An oligonucleotide sequence according to claim 1 wherein the 5'terminus is modified.

4. An oligonucleotide sequence according to claim 1 wherein a modification at the 5' terminus is selected from the group consisting of amino acids, digoxigenin labelling, biotin labelling and additional nucleotides.

5. An oligonucleotide sequence according to claim 4 wherein said additional nucleotides comprise one or more restriction sites for restriction enzyme recognition.

6. An oligonucleotide sequence according to claim 1 wherein said oligonucleotide sequence exhibits a homology of $\geq 95\%$ to one or more sequences according to claim 1.

7. An oligonucleotide sequence according to claim 1, wherein said oligonucleotide sequence is contained in a vector system.

8. An oligonucleotide sequence according to claim 7, wherein said vector is a plasmid.

9. A method for performing an IL-PCR, comprising the following steps:
   (a) preparing a PCR reaction mix comprising DNA to be analyzed and one or more oligonucleotides having a sequence according to claim 1;
   (b) performing amplification steps on said reaction mix comprising several denaturations and renaturations to obtain amplified DNA products; and
   (c) separating and analyzing said amplification products.

10. A method according to claim 9, wherein said amplification steps comprise one initial denaturation step, one or more low stringency denaturations and renaturations and one or more higher stringency denaturations and renaturations, and a final chain elongation step.

11. A method according to claim 9, wherein 3–7 low stringency denaturation and renaturation steps and 20–30 higher stringency denaturation and renaturation steps are performed.

12. A method according to claim 9, wherein viscosity increasing agents are added.

13. A method according to claim 12, wherein said agent is gelatin.

14. A method according to claim 9, wherein the DNA to be analyzed is isolated from a member of the group consisting of prokarya, archaea and eukarya and genetically altered variations thereof.

15. A method according to claim 9, wherein the DNA to be analyzed is DNA from normal cells or transformed cells.

16. A method according to claim 9, wherein the DNA to be analyzed is DNA from yeasts or bacteria.

17. The method of claim 9, wherein said method discriminates between DNA of members of the group consisting of prokarya, archaea, eukarya and genetically altered organisms thereof.

18. The method of claim 17, wherein said method discriminates between individual taxa and phyla of members of the group consisting of prokarya, archaea and eukarya.

19. The method of claim 9, wherein said method discriminates between yeast and bacteria.

20. The method of claim 9, wherein said method discriminates normal cells from tumor cells.

21. The method of claim 9, wherein said method identifies prokaryotic or eukaryotic organisms.

22. The method of claim 9, wherein said method results in a taxonomic characterization of prokaryotic or eukaryotic organisms.

23. The method of claim 9, wherein said method results in the construction or identification of transformation in tumor markers.

24. The method of claim 9, wherein said method is a tumor diagnostic.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA oligonucleotide,
            consensus sequence of sequences of several clones"

( i i i ) HYPOTHETICAL: NO ( i v ) ANTI-SENSE: NO ( v i ) ORIGINAL SOURCE:
        ( A ) ORGANISM: Mesocricetus auratus
        ( G ) CELL TYPE: Embryofibroblast ( x i ) SEQUENCE DESCRIPTION: SEQ ID NO: 1:

GAAGGGTCTT TGCCAAACTC                                                   2 0

( 2 ) INFORMATION FOR SEQ ID NO: 2:

( i ) SEQUENCE CHARACTERISTICS:
        ( A ) LENGTH: 20 base pairs
        ( B ) TYPE: nucleic acid
        ( C ) STRANDEDNESS: single ( D ) TOPOLOGY: linear ( i i ) MOLECULE TYPE: other nucleic acid
            ( A ) DESCRIPTION: /desc = "DNA oligonucleotide,
                    consensus sequence of sequences of several clones"

( i i i ) HYPOTHETICAL: NO ( i v ) ANTI-SENSE: NO ( v i ) ORIGINAL SOURCE:
            ( A ) ORGANISM: Mesocricetus auratus
            ( G ) CELL TYPE: Embryofibroblast ( x i ) SEQUENCE DESCRIPTION: SEQ ID NO: 2:

GAGTTTGGCA AAGACCCTTC        20

( 2 ) INFORMATION FOR SEQ ID NO: 3:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "DNA oligonucleotide,
                    consensus sequence of sequences of several clones"

( i i i ) HYPOTHETICAL: NO ( i v ) ANTI-SENSE: NO ( v i ) ORIGINAL SOURCE:
            ( A ) ORGANISM: Mesocricetus auratus
            ( G ) CELL TYPE: Embryofibroblast ( x i ) SEQUENCE DESCRIPTION: SEQ ID NO: 3:

CCATGTCTAT CTCCATGCAC        20

( 2 ) INFORMATION FOR SEQ ID NO: 4:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "DNA oligonucleotide,
                    consensus sequence of sequences of several clones"

( i i i ) HYPOTHETICAL: NO ( i v ) ANTI-SENSE: NO ( v i ) ORIGINAL SOURCE:
            ( A ) ORGANISM: Mesocricetus auratus
            ( G ) CELL TYPE: Embryofibroblast ( x i ) SEQUENCE DESCRIPTION: SEQ ID NO: 4:

GTGCATGGAG ATAGACATGG        20

( 2 ) INFORMATION FOR SEQ ID NO: 5:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "DNA oligonucleotide,
                    consensus sequence of sequences of several clones"

```
(  i i i  ) HYPOTHETICAL: NO (  i v  ) ANTI-SENSE: NO (  v i  ) ORIGINAL SOURCE:
           ( A ) ORGANISM: Mesocricetus auratus
           ( G ) CELL TYPE: Embryofibroblast (  x i  ) SEQUENCE DESCRIPTION: SEQ ID NO: 5:

GGCTGCCTTT ATATGTTACT GGCC                                                24

( 2 ) INFORMATION FOR SEQ ID NO: 6:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "DNA oligonucleotide,
                     consensus sequence of sequences of several clones"

( i i i ) HYPOTHETICAL: NO ( i v ) ANTI-SENSE: NO ( v i ) ORIGINAL SOURCE:
              ( A ) ORGANISM: Mesocricetus auratus
              ( G ) CELL TYPE: Embryofibroblast ( x i ) SEQUENCE DESCRIPTION: SEQ ID NO: 6:

GGAGTGCTGA CTCATACAGC CTCC                                                24

( 2 ) INFORMATION FOR SEQ ID NO: 7:

( i ) SEQUENCE CHARACTERISTICS:
              ( A ) LENGTH: 23 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "DNA oligonucleotide,
                     consensus sequence of sequences of several clones"

( i i i ) HYPOTHETICAL: NO ( i v ) ANTI-SENSE: NO ( v i ) ORIGINAL SOURCE:
              ( A ) ORGANISM: Mesocricetus auratus
              ( G ) CELL TYPE: Embryofibroblast ( x i ) SEQUENCE DESCRIPTION: SEQ ID NO: 7:

CCTGTCTAGT GGTGAGAGTG GTG                                                 23
```